(12) United States Patent
Park et al.

(10) Patent No.: US 10,247,685 B2
(45) Date of Patent: Apr. 2, 2019

(54) HIGH-TEMPERATURE STRUCTURE FOR MEASURING PROPERTIES OF CURVED THERMOELECTRIC DEVICE, AND SYSTEM AND METHOD FOR MEASURING PROPERTIES OF CURVED THERMOELECTRIC DEVICE USING THE SAME

(71) Applicants: KOREA INSTITUTE OF ENERGY RESEARCH, Daejeon (KR); KOREA ADVANCED INSTITUTE OF SCIENCE AND TECHNOLOGY, Daejeon (KR)

(72) Inventors: Sang Hyun Park, Daejeon (KR); Chung-Yul Yoo, Daejeon (KR); Hong Soo Kim, Daejeon (KR); Min Soo Suh, Daejeon (KR); Dong Kook Kim, Daejeon (KR); Byung jin Cho, Daejeon (KR)

(73) Assignees: KOREA INSTITUTE OF ENERGY RESEARCH, Daejeon (KR); KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 145 days.

(21) Appl. No.: 15/219,429

(22) Filed: Jul. 26, 2016

(65) Prior Publication Data

US 2017/0205364 A1   Jul. 20, 2017

(30) Foreign Application Priority Data

Jan. 28, 2016   (KR) ........................ 10-2016-0010700

(51) Int. Cl.
*G01N 25/18* (2006.01)
(52) U.S. Cl.
CPC .................................... *G01N 25/18* (2013.01)
(58) Field of Classification Search
CPC combination set(s) only.
See application file for complete search history.

(56) References Cited

U.S. PATENT DOCUMENTS

| 6,306,673 | B1 * | 10/2001 | Imanishi | ............... | H01L 35/325 |
| | | | | | 136/201 |
| 2001/0052246 | A1 * | 12/2001 | Kamata | ................. | C03B 29/025 |
| | | | | | 65/29.19 |

(Continued)

FOREIGN PATENT DOCUMENTS

| JP | 06-159936 A | 6/1994 |
| JP | 2002-511939 A | 4/2002 |

(Continued)

*Primary Examiner* — Lisa Caputo
*Assistant Examiner* — Nasir U Ahmed
(74) *Attorney, Agent, or Firm* — Sughrue Mion, PLLC

(57) ABSTRACT

Disclosed herein are a high-temperature structure for measuring properties of a curved thermoelectric device, which is capable of precisely measuring the properties of a medium-temperature curved thermoelectric device that is applied to a tube-type waste heat source and is used in research, and a system and a method for measuring the properties using the same. The high-temperature structure may include a plurality of rod-shaped cartridge heaters, and a heating element having a surface that is a curved surface coming into contact with a lower end of the curved thermoelectric device, having a plurality of holes for accommodating the plurality of cartridge heaters, and directly heating the lower end of the curved thermoelectric device.

9 Claims, 11 Drawing Sheets

(56) References Cited

U.S. PATENT DOCUMENTS

2007/0220902 A1* 9/2007 Matsuoka ............... H01L 35/30
                                                                    62/3.3
2011/0209740 A1* 9/2011 Bell ....................... H01L 35/30
                                                                    136/224

FOREIGN PATENT DOCUMENTS

| | | |
|---|---|---|
| JP | 2005-129784 A | 5/2005 |
| JP | 2007-59462 A | 3/2007 |
| KR | 20-1998-0016273 A | 6/1998 |
| KR | 1020110130760 A | 12/2011 |
| KR | 10-2015-0007686 A | 1/2015 |
| KR | 1020150007686 A | 1/2015 |
| KR | 10-2015-0037458 A | 4/2015 |

* cited by examiner

HIGH-TEMPERATURE STRUCTURE FOR MEASURING PROPERTIES OF CURVED THERMOELECTRIC DEVICE, AND SYSTEM AND METHOD FOR MEASURING PROPERTIES OF CURVED THERMOELECTRIC DEVICE USING THE SAME

CROSS-REFERENCE TO RELATED APPLICATION

This application claims the priority benefit of Korean Patent Application No. 10-2016-0010700, filed on Jan. 18, 2016 in the Korean Intellectual Property Office, the disclosure of which is incorporated herein by reference.

BACKGROUND OF THE INVENTION

1. Field of the Invention

The present invention relates generally to a high-temperature structure for measuring properties of a curved thermoelectric device, and a system and a method for measuring the properties using the same. More particularly, the present invention relates to a high-temperature structure for measuring properties of a curved thermoelectric device, which is capable of precisely measuring the properties of a medium-temperature curved thermoelectric device that is applied to a tube-type waste heat source and is used in research, and to a system and a method for measuring the properties using the same.

2. Description of the Related Art

For decades, it has been reported that thermoelectric generation technology, also known as low-efficient energy conversion technology, may have efficiency of 10% or more in a region of medium temperature (300 to 700° C.). Further, thermoelectric generation technology is appealing as a new energy regeneration technology, and is being actively researched around the world.

As illustrated in FIG. 1A, a general thermoelectric module is usually manufactured to be in a flat shape. However, in recent years, in order to apply the thermoelectric module directly to a pipe where a large quantity of waste heat is generated, namely, to a tube-type waste heat source, those skilled in the art have shown interest in the manufacture of a curved thermoelectric module, as illustrated in FIG. 1B.

In order to develop the above-mentioned thermoelectric module, it is necessary to precisely measure the properties of the thermoelectric module. However, a conventional thermoelectric-module measuring apparatus is problematic in that it is possible to measure only a flat thermoelectric module, as described in Korean Patent Application Publication No. 10-2015-0007686, so that the properties of the curved thermoelectric module cannot be measured.

SUMMARY OF THE INVENTION

Accordingly, the present invention has been made keeping in mind the above problems occurring in the related art, and the present invention is intended to propose a high-temperature structure for measuring properties of a curved thermoelectric device, and a system and a method for measuring the properties using the same, in which a contact surface between the thermoelectric device is formed into a curved surface and a surface temperature of the high-temperature structure is kept uniform, thus being capable of precisely measuring the properties of the curved thermoelectric device.

In order to accomplish the above object, the present invention is intended to propose a high-temperature structure for measuring properties of a curved thermoelectric device, the high-temperature structure including a plurality of rod-shaped cartridge heaters; and a heating element having a surface that is a curved surface coming into contact with a lower end of the curved thermoelectric device, having a plurality of holes for accommodating the plurality of cartridge heaters, and directly heating the lower end of the curved thermoelectric device.

The plurality of holes may include a plurality of first holes that have the same distance from a center to the surface.

Further, the plurality of cartridge heaters may include a plurality of first rod-shaped cartridge heaters each having a first diameter; and a plurality of second rod-shaped cartridge heaters each having a second diameter that is smaller than the first diameter, wherein the plurality of holes may include a plurality of second holes accommodating the plurality of first rod-shaped cartridge heaters; and a plurality of third holes placed above the plurality of second holes to be located therebetween, and accommodating the plurality of second rod-shaped cartridge heaters.

The high-temperature structure may further include a heat flow meter measuring heat conductivity distribution of heat that is outputted from the plurality of cartridge heaters; a temperature sensor measuring surface temperature distribution of the heating element; and a feedback control receiving the heat conductivity distribution and the surface temperature distribution, and controlling heat-generation temperature of the plurality of cartridge heaters such that the heat conductivity distribution and the surface temperature distribution are uniform.

In order to accomplish the above object, the present invention is intended to propose a system for measuring properties of a curved thermoelectric device, the system including a low-temperature section having a surface that is a curved surface coming into contact with an upper end of the curved thermoelectric device, and directly cooling the upper end of the curved thermoelectric device; a plurality of cartridge heaters each having a rod shape; a heating element having a surface that is a curved surface coming into contact with a lower end of the curved thermoelectric device, having a plurality of holes for accommodating the plurality of cartridge heaters, and directly heating the lower end of the curved thermoelectric device; a shielding section surrounding the heating element; a heat-insulation section disposed on a lower end of the heating element and made of a heat insulation material; and a measuring section connected with both the low-temperature section and the heating element to measure thermoelectric performance of the curved thermoelectric device.

The plurality of holes may include a plurality of first holes that have the same distance from a center to the surface.

The plurality of cartridge heaters may include a plurality of first rod-shaped cartridge heaters each having a first diameter; and a plurality of second rod-shaped cartridge heaters each having a second diameter that is smaller than the first diameter, wherein the plurality of holes may include a plurality of second holes accommodating the plurality of first rod-shaped cartridge heaters; and a plurality of third holes placed above the plurality of second holes to be located therebetween, and accommodating the plurality of second rod-shaped cartridge heaters.

The system may further include a heat flow meter measuring heat conductivity distribution of heat that is outputted from the plurality of cartridge heaters; a temperature sensor measuring surface temperature distribution of the heating element; and a feedback control receiving the heat conductivity distribution and the surface temperature distribution, and controlling heat-generation temperature of the plurality of cartridge heaters such that the heat conductivity distribution and the surface temperature distribution are uniform.

The shielding section may have a curved frame structure to surround an upper portion of a side of the heating element.

In order to accomplish the above object, the present invention is intended to propose a method for measuring properties using a high-temperature structure for measuring properties of a curved thermoelectric device, using a heating element that has a surface that is a curved surface coming into contact with a lower end of the curved thermoelectric device, has a plurality of holes for accommodating the plurality of cartridge heaters, and directly heats the lower end of the curved thermoelectric device, the method including measuring surface temperature distribution of the heating element; measuring heat conductivity distribution of heat that is outputted from the plurality of cartridge heaters; receiving the heat conductivity distribution and the surface temperature distribution, and controlling heat-generation temperature of the plurality of cartridge heaters such that the heat conductivity distribution and the surface temperature distribution are uniform; directly cooling an upper end of the curved thermoelectric device, and directly heating a lower end of the curved thermoelectric device using the heating element; and measuring thermoelectric performance of the curved thermoelectric device.

As described above, the present invention provides a high-temperature structure for measuring properties of a curved thermoelectric device, and a system and a method for measuring the properties using the same, in which a heating element having a curved surface for forming a heat contact state is provided in measuring the properties of the curved thermoelectric device, and various heater arrangements are provided using a rod-shaped cartridge heater, thus keeping the surface temperature of the high-temperature structure that is the heating element uniform, and thereby allowing the properties of the curved thermoelectric device to be precisely measured.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF PREFERRED EMBODIMENTS

Hereinafter, reference will now be made in detail to various embodiments of the present invention. While the invention will be described in conjunction with exemplary embodiments, it will be understood that the present description is not intended to limit the invention to those exemplary embodiments. On the contrary, the invention is intended to cover the exemplary embodiments as well as various alternatives, modifications, equivalents and other embodiments; which may be included within the spirit and scope of the invention as defined by the appended claims.

The meaning of terms used herein should be understood as follows.

Terms such as 'first' and 'second' may be used to describe various components, but they should not limit the various components. For example, a first component may be referred to as a second component, and a second component may be referred to as a first component.

It is also noted that in this specification, "connected/coupled" refers to one component not only directly coupling another component but also indirectly coupling another component through an intermediate component. On the other hand, "directly connected/directly coupled" refers to one component directly coupling another component without an intermediate component. Meanwhile, the same applies to other expressions describing a relationship between components, for example, "between", "directly between", or "adjacent to" and "directly adjacent to", etc.

The singular forms "a" and "an" include plural referents unless the context clearly dictates otherwise. Further, it should be understood that terms "comprise", "comprises", "comprising" or the like are inclusive of characteristics, numerals, steps, operations, components, parts or combination thereof, which are described herein, but are not exclusive of one or more different characteristics, numerals, steps, operations, components, parts or combination thereof.

The steps may be performed in an order different from a specified order unless the context clearly dictates otherwise. The steps may be performed in the same order as the specified order or in reverse order.

The terms or words used in the description and the claims of the present invention should not be interpreted as being limited merely to common and dictionary meanings. On the contrary, they should be interpreted based on the meanings and concepts of the invention in keeping with the scope of the invention on the basis of the principle that the inventor(s) can appropriately define the terms in order to describe the invention in the best way.

Figure 1A:
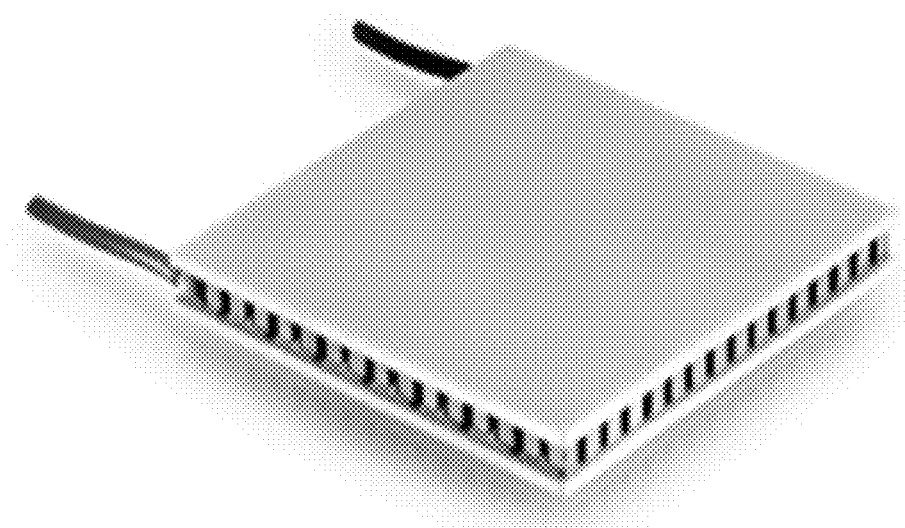
FIGS. 1A and 1B are views illustrating expected structures of a flat thermoelectric module and a curved thermoelectric module.
Figure 1B:
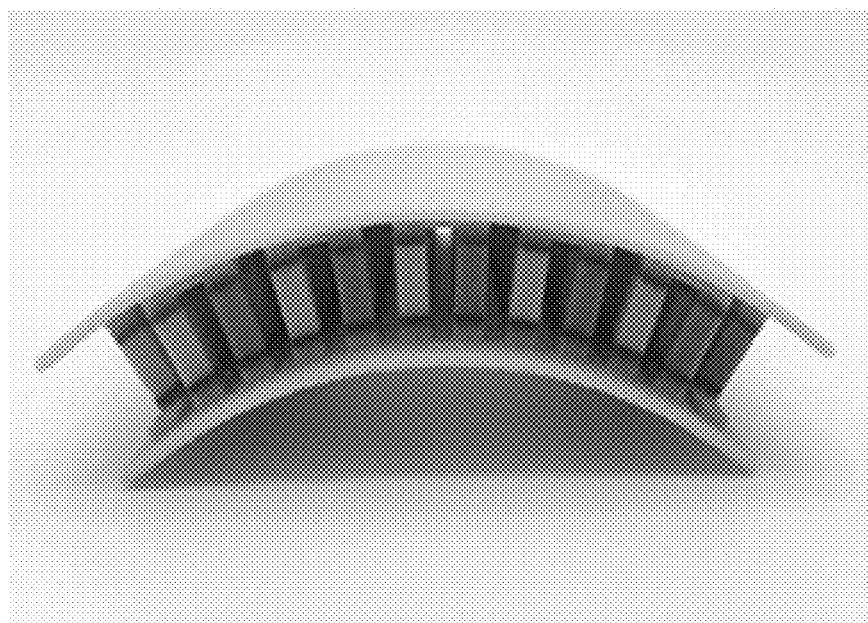
Figure 2:
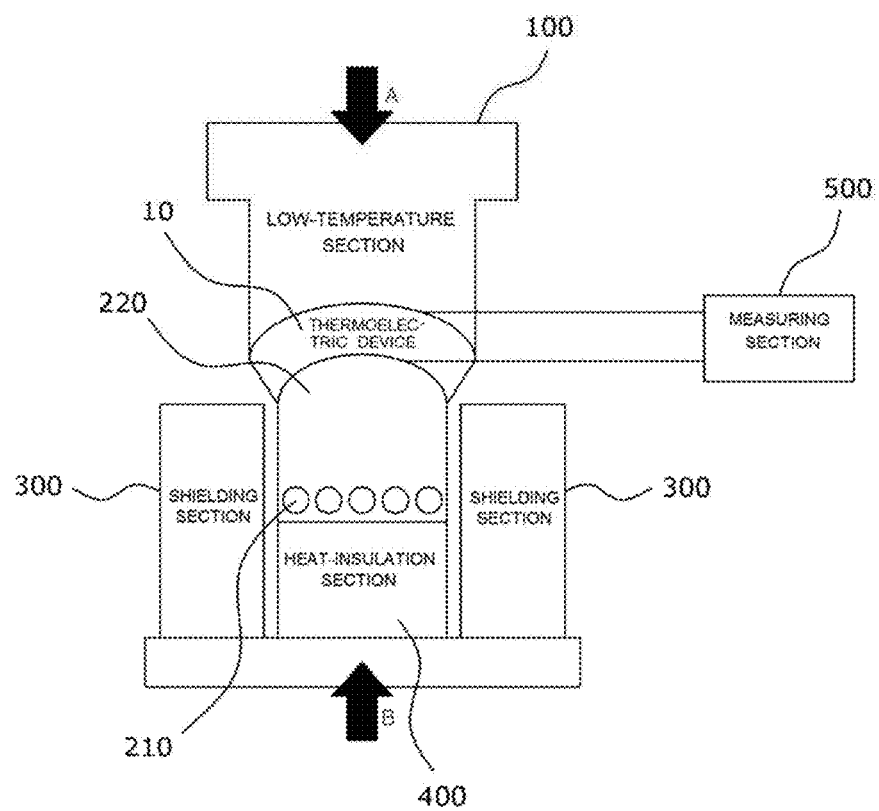
FIG. 2 is a view illustrating a properties measuring system using a high-temperature structure for measuring properties of a curved thermoelectric device according to an embodiment of the present invention.

FIG. 2 is a view illustrating a properties measuring system using a high-temperature structure for measuring properties of a curved thermoelectric device according to an embodiment of the present invention. The properties measuring system using the high-temperature structure for measuring properties of the curved thermoelectric device according to the embodiment of the present invention may include a low-temperature section 100, a cartridge heater 210, a heating element 220, a shielding section 300, a heat-insulation section 400, and a measuring section 500.

The low-temperature section 100 is aligned with the heating element 220 to fix a curved thermoelectric device 10 that is to be measured, and is provided with a surface that is a curved surface coming into contact with an upper end of the curved thermoelectric device 10. The low-temperature section 100 may directly cool the upper end of the curved thermoelectric device 10 in a Peltier cooling method or the like. However, the surface coming into contact with the upper end of the curved thermoelectric device 10 may be continuously cooled using coolant or air circulation, without being limited to the above-mentioned method.

Further, the heating element 220 has a surface that is a curved surface coming into contact with a lower end of the curved thermoelectric device 10, has a plurality of holes for accommodating a plurality of cartridge heaters 210, and directly heats the lower end of the curved thermoelectric device 10. Here, the heating element 220 is preferably a block made of a copper (Cu) material having good heat conductivity. However, it is possible to adopt any material such as tin/copper (Sn/Cu) alloy, without being limited to the copper material.

In order to cause the low-temperature section 100 and the heating element 220 to come into close contact with the upper and lower ends of the curved thermoelectric device 10, respectively, it is preferable to apply external force A and B such as elastic force from a side opposite to a side coming into contact with the curved thermoelectric device 10 towards the curved thermoelectric device 10.

Further, the cartridge heaters 210 cause the heating element 220 to generate heat, and preferably have a rod shape to facilitate replacement and realize various arrangements.

The shielding section 300 surrounds the heating element 220 to shield convection and radiation heat, thus allowing the measuring section 500 to precisely measure the properties of the curved thermoelectric device 10.

The heat-insulation section 400 has heat insulation properties, is disposed on the lower end of the heating element 220, and serves to insulate heat from the heating element 220.

The measuring section 500 is connected with the low-temperature section 100 and the heating element 220 to measure the thermoelectric performance of the curved thermoelectric device 10. Here, the measuring section 500 may measure the temperature, the current and the voltage on the upper and lower ends of the curved thermoelectric device 10 so as to measure the thermoelectric performance. That is, the thermoelectric performance for evaluating the thermoelectric conversion properties of the thermoelectric device may be evaluated through the thermoelectric figure of merit (Z, 1/K) that is calculated by the following Equation 1.

$$Z = \frac{\alpha^2}{\rho} \cdot \lambda \quad \text{[Equation 1]}$$

In this equation, $\alpha$ represents a Seebeck coefficient (V/K), $\rho$ represents a resistivity ($\Omega \cdot m$), and $\lambda$ represents a heat conductivity (W/m·K).

In order to precisely measure the thermoelectric performance, the temperature on the surface of the heating element 220 that is in direct contact with the thermoelectric module should be precisely maintained as desired, and the temperature distribution throughout the entire surface of the heating element 220 should be uniform.

FIGS. 3A to 3D are views illustrating an embodiment of the high-temperature structure for measuring the properties of the curved thermoelectric device according to the embodiment of the present invention. These drawings illustrate various arrangements of the cartridge heaters 210 that are accommodated in the heating element 220 to make the temperature on the surface of the heating element 220 uniform.

That is, the surface coming into contact with the lower end of the curved thermoelectric device 10 of the heating element 220 has the shape of a curved surface, namely, a cylindrical side surface. Thus, if the cartridge heaters 210 are arranged in a single linear shape in the heating element 220, a difference in temperature between a central portion and an edge portion on a surface of the heating element 220 may occur.

Figure 3A:
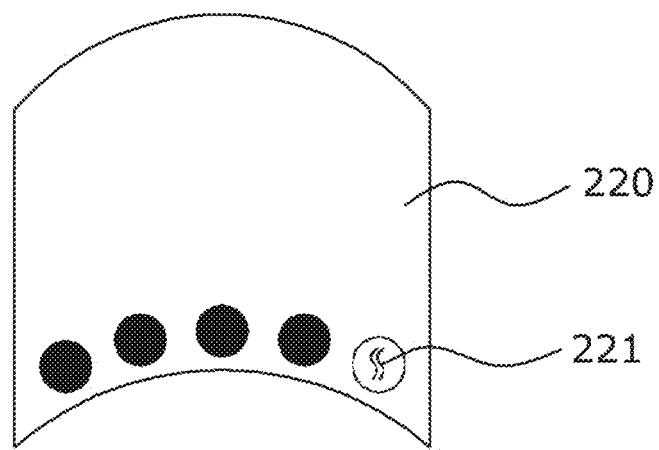
FIGS. 3A, 3B, 3C and 3D are views illustrating an embodiment of the high-temperature structure for measuring the properties of the curved thermoelectric device according to the embodiment of the present invention.

First, referring to FIG. 3A, the heating element 220 may have a plurality of first holes 221 that have the same distance from the center to the surface coming into contact with the lower end of the curved thermoelectric device 10 of the heating element 220 so as to eliminate the difference in temperature between the central portion and the edge portion on the surface of the heating element 220.

Figure 3B:
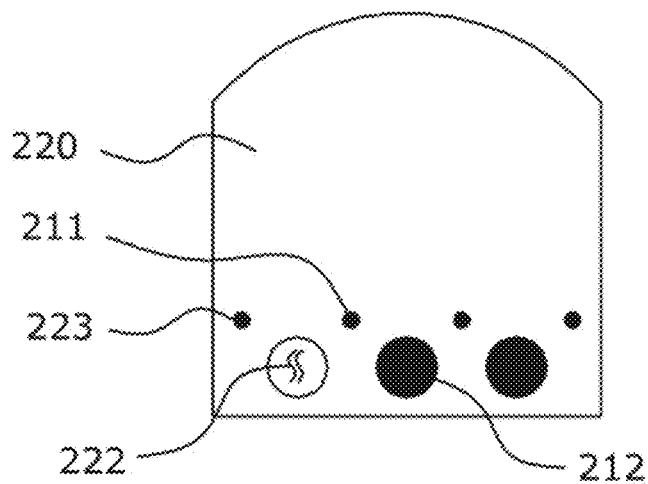

Referring to FIG. 3B, the plurality of cartridge heaters 210 may be classified into two kinds, namely, a plurality of first rod-shaped cartridge heaters 212 each having a first diameter, and a plurality of second rod-shaped cartridge heaters 211 each having a second diameter that is smaller than the first diameter. A plurality of second holes 222 that accommodate the first rod-shaped cartridge heaters 212 and a plurality of third holes 223 that are placed above the second holes 222 to be located therebetween to accommodate the second rod-shaped cartridge heaters 211 may be formed in the heating element 220. That is, a desired temperature may be roughly achieved by the first rod-shaped cartridge heaters 212 each having a large diameter, and then the surface temperature of the heating element 220 may be uniformly adjusted by arranging the second rod-shaped cartridge heaters 211 each having a small diameter between the first rod-shaped cartridge heaters 212.

Figure 3C:
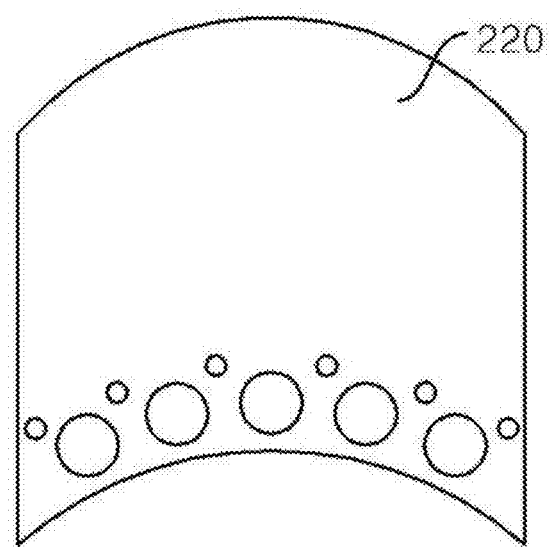
Figure 3D:
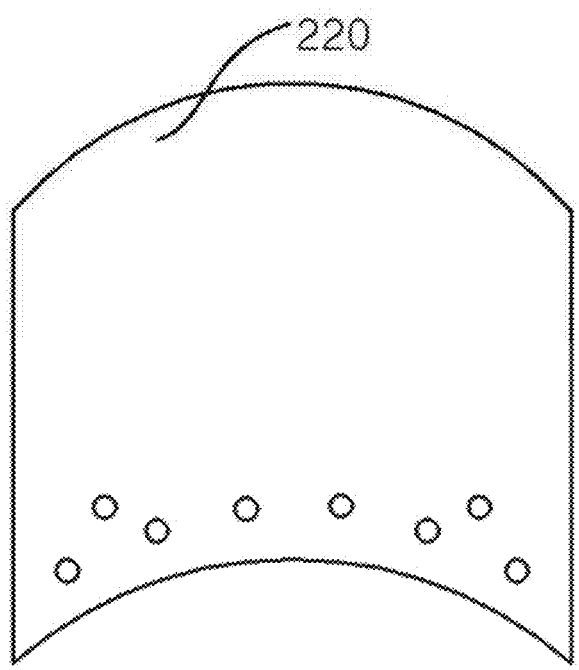

Meanwhile, as illustrated in FIGS. 3C and 3D, there may be present various arrangements of the cartridge heaters 210 that have various sizes to make the surface temperature of the heating element 220 uniform. This causes the temperature distribution on the surface of the curved heating element 220 to be constant, thus allowing the thermoelectric performance to be delicately measured.

Figure 4A:
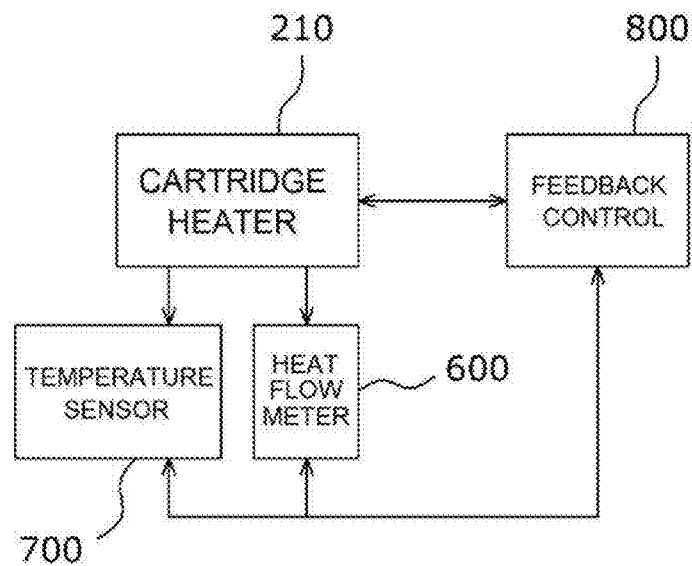
FIGS. 4A and 4B are views illustrating another embodiment of the high-temperature structure for measuring the properties of the curved thermoelectric device according to the embodiment of the present invention.
Figure 4B:
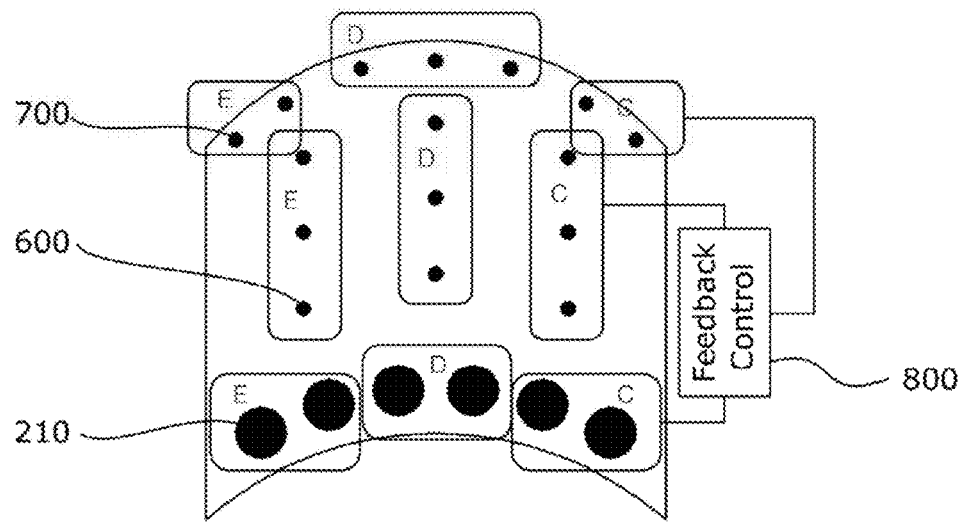

FIGS. 4A and 4B are views illustrating another embodiment of the high-temperature structure for measuring the properties of the curved thermoelectric device according to the embodiment of the present invention. The high-temperature structure for measuring the properties of the curved thermoelectric device of the present invention may further include a heat flow meter 600, a temperature sensor 700, and a feedback control 800.

The heat flow meter 600 measures the heat conductivity distribution of heat that is outputted from the plurality of cartridge heaters 210, and then transmits the measured heat conductivity distribution to the feedback control 800. That is, in order to measure efficiency, the heat conduction of the heating element 220 is measured.

Further, the temperature sensor 700 detects the surface temperature distribution of the heating element 220, and then transmits the detected surface temperature distribution to the feedback control 800. A plurality of temperature sensors 700 may be arranged and used as the heat flow meter 600. However, the invention is not limited thereto.

The feedback control 800 receives the heat conductivity distribution that is inputted from the heat flow meter 600, receives the surface temperature distribution that is inputted from the temperature sensor 700, analyzes the inputted heat conductivity distribution and surface temperature distribution, and controls the heat-generating temperature of the cartridge heaters 210 so that the heat conductivity distribution and the surface temperature distribution become uniform. For convenience, in FIG. 4B, the feedback control 800 is connected to only the heat flow meter 600, the temperature sensor 700, and the cartridge heater 210 that are disposed in a predetermined region C. However, the feedback control 800 of the present invention may transmit and receive a signal to and from the heat flow meter 600, the temperature sensor 700, and the cartridge heater 210 all which are disposed in other regions E and D.

In order to cause the surface temperature of the heating element 220 to reach a desired temperature, the plurality of cartridge heaters 210 generates heat. However, the surface temperature of the heating element 220 may be non-uniform. In order to solve the problem, as illustrated in FIG. 4B, temperature sensors 700 may be arranged around the surfaces of the plurality of heating elements 220 to detect surface temperatures for predetermined regions, for example, three regions C, D and E as illustrated in FIG. 4B and adjust the degree to which the cartridge heaters 210 generate heat, based on the distribution of the surface temperature measured by and inputted from the feedback control 800.

For example, when the temperature of the central region D in the surface of the heating element 220 is higher than that of the edge, the feedback control 800 regulates the degree to which the cartridge heaters 210 disposed in the edge regions C and E generate heat so that the heat-generation degree is gradually increased. Such a regulating process may be performed until the temperature measured by the temperature sensor 700 in the central region D becomes equal to the temperature measured by the temperature sensors 700 in the edge regions C and E.

Meanwhile, if the above-described feedback process of the feedback control 800 is performed so as to cause the surface temperature of the heating element 220 to be uniform, the heat-generating quantities of the cartridge heaters 210 are different from each other, and consequently the heat conductivities of the regions C, D and E in the heating element 220 are likewise different from each other. However, when the thermoelectric performance of the curved thermoelectric device 10 is measured, a heat conduction quantity applied to the curved thermoelectric device 10 should be constant to allow the thermoelectric performance to be precisely measured. Therefore, as illustrated in FIG. 4B, the heat flow meter 600 is disposed around the lower ends of the plurality of temperature sensors 700, and measures heat conductivities for predetermined regions, for example, three regions C, D and E, respectively, as in FIG. 4B. The heat flow meter 600 receives the distribution of the heat conductivity that is measured by and inputted from the feedback control 800 to adjust the degree to which the cartridge heaters 210 generates heat.

That is, the feedback control 800 may function to maintain environment that is suitable to measure the thermoelectric performance of the curved thermoelectric device 10, in other words, uniform surface temperature and heat conductivity distribution.

Figure 5:
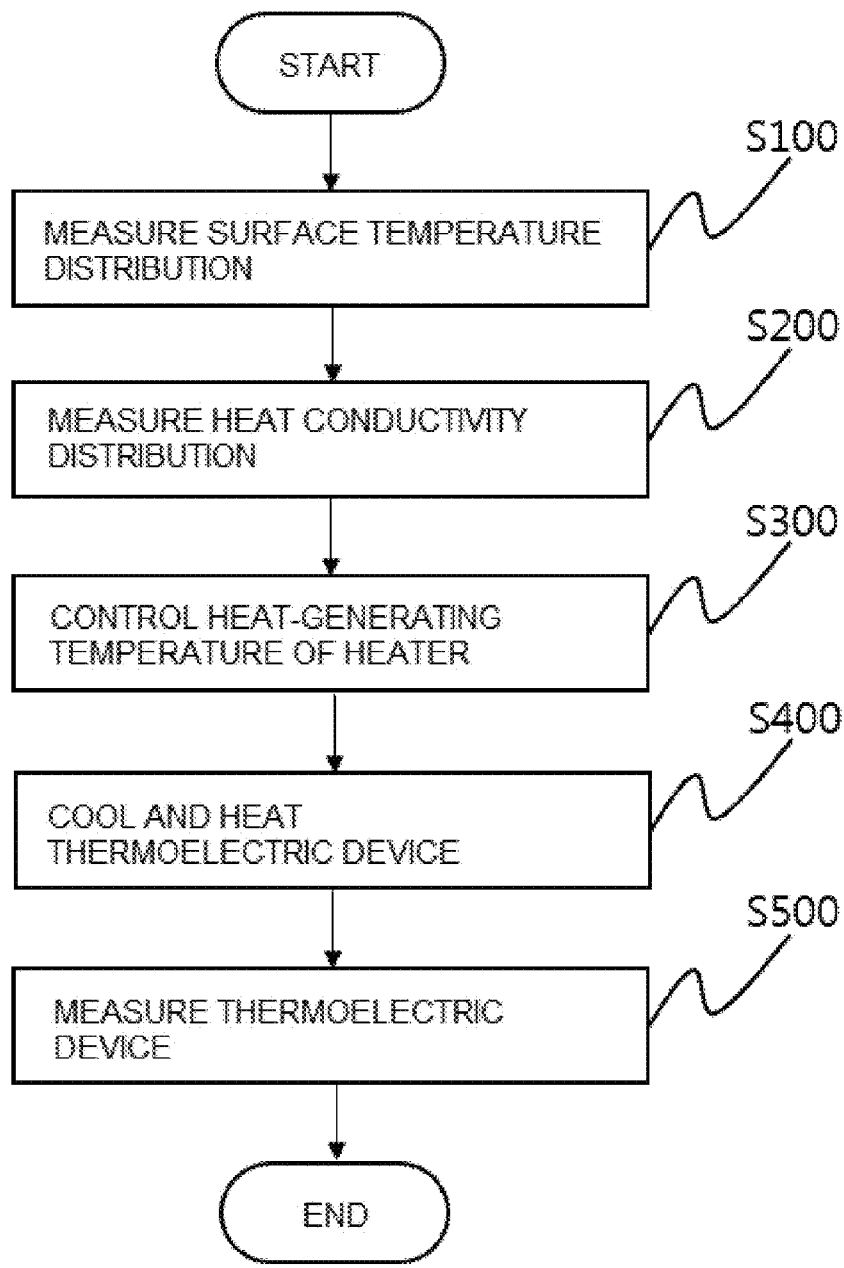
FIG. 5 is a view illustrating a method for measuring properties using a high-temperature structure for measuring properties of a curved thermoelectric device according to an embodiment of the present invention.

FIG. 5 is a view illustrating a method for measuring properties using a high-temperature structure for measuring properties of a curved thermoelectric device according to an embodiment of the present invention. The properties measuring method using the high-temperature structure for measuring the properties of the curved thermoelectric device according to the embodiment of the present invention will be described below with reference to FIGS. 2 to 5.

First, in order to reach a desired surface temperature of the heating element 220, the plurality of cartridge heaters 210 generates heat, the surface temperature distribution of the heating element 220 is measured by the temperature sensor 700, and then the measured surface temperature distribution is transmitted to the feedback control 800, at S100.

Next, the heat flow meter 600 measures the heat conductivity distribution of the heat outputted from the plurality of cartridge heaters 210, and outputs the measured heat conductivity distribution to the feedback control 800, at S200.

Subsequently, the feedback control 800 receives the heat conductivity distribution and the surface temperature distribution that are inputted from the heat flow meter 600 and the temperature sensor 700, and controls the heat generation temperature of the plurality of cartridge heaters 210 such that the heat conductivity distribution and the surface temperature distribution are uniform, at S300.

Next, the curved thermoelectric device 10 is interposed between the low-temperature section 100 and the heating element 220, so that the upper end of the curved thermoelectric device 10 is directly cooled using the low-temperature section 100 and the lower end of the curved thermoelectric device 10 is directly heated using the heating element 220, at S400.

Subsequently, the measuring section 500 measures the thermoelectric performance of the curved thermoelectric device 10, at S500. In this regard, the measuring section 500 may measure the temperature, the current, the voltage and the like of the upper and lower ends of the curved thermoelectric device 10 to measure the thermoelectric performance.

Figure 6:
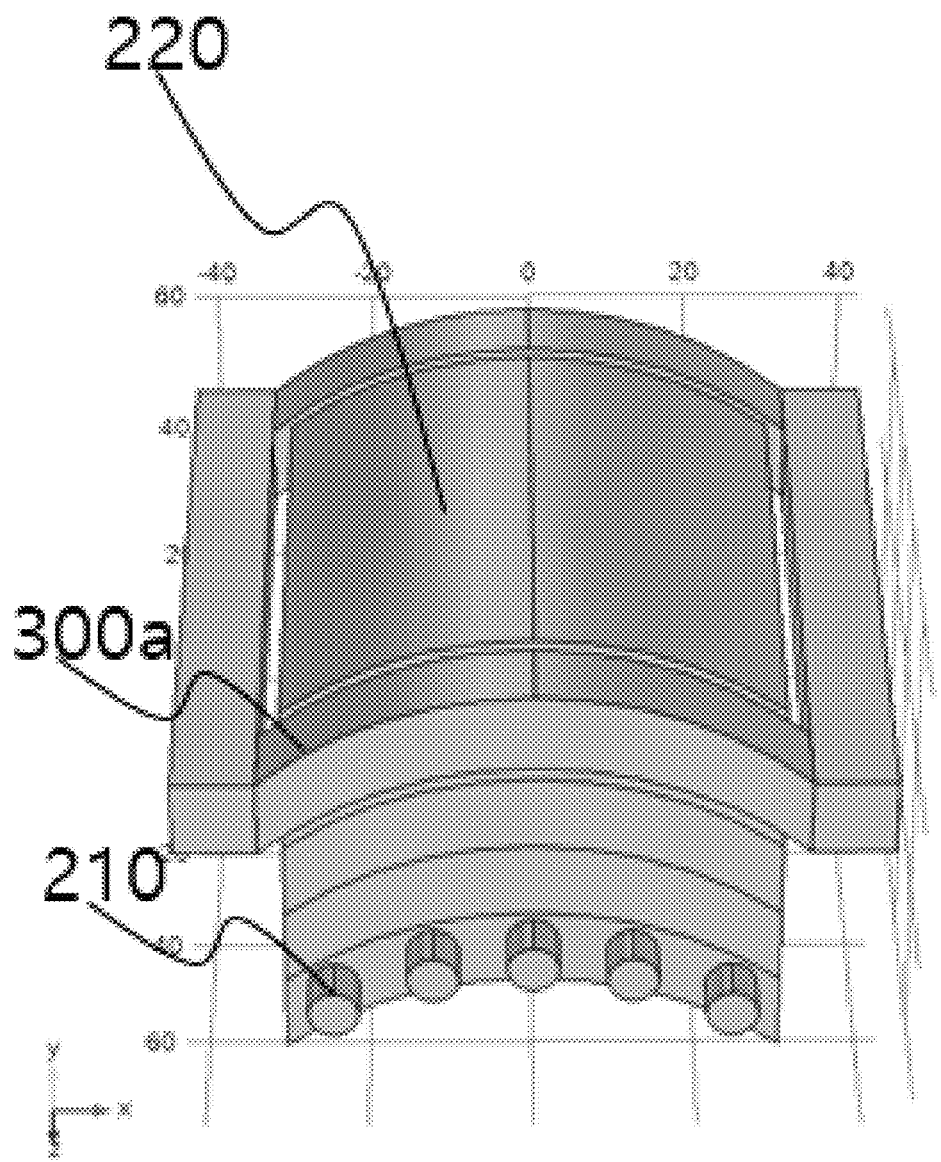
FIG. 6 is a view illustrating an embodiment of a shielding section in a properties measuring system using the high-temperature structure for measuring the properties of the curved thermoelectric device according to the embodiment of the present invention.
Figure 7A:
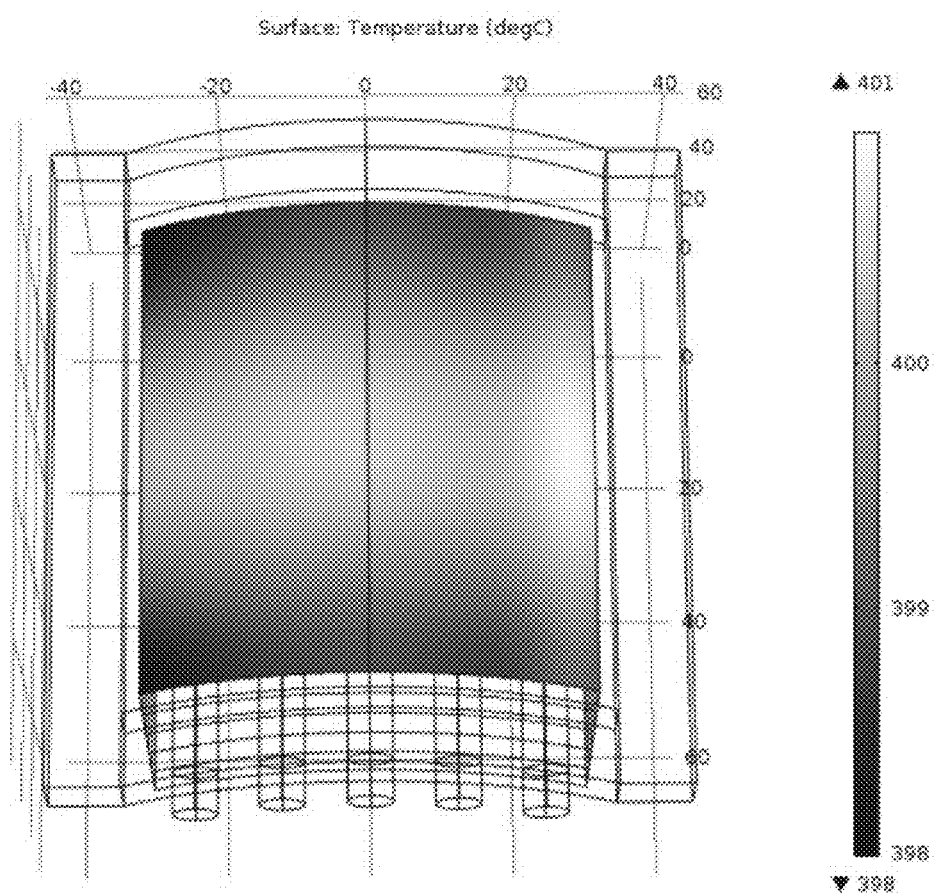
FIGS. 7A and 7B are views illustrating the distribution of a surface temperature and a surface heat flux of the high-temperature structure for measuring the properties of the curved thermoelectric device to which the shielding section of FIG. 6 is applied.
Figure 7B:
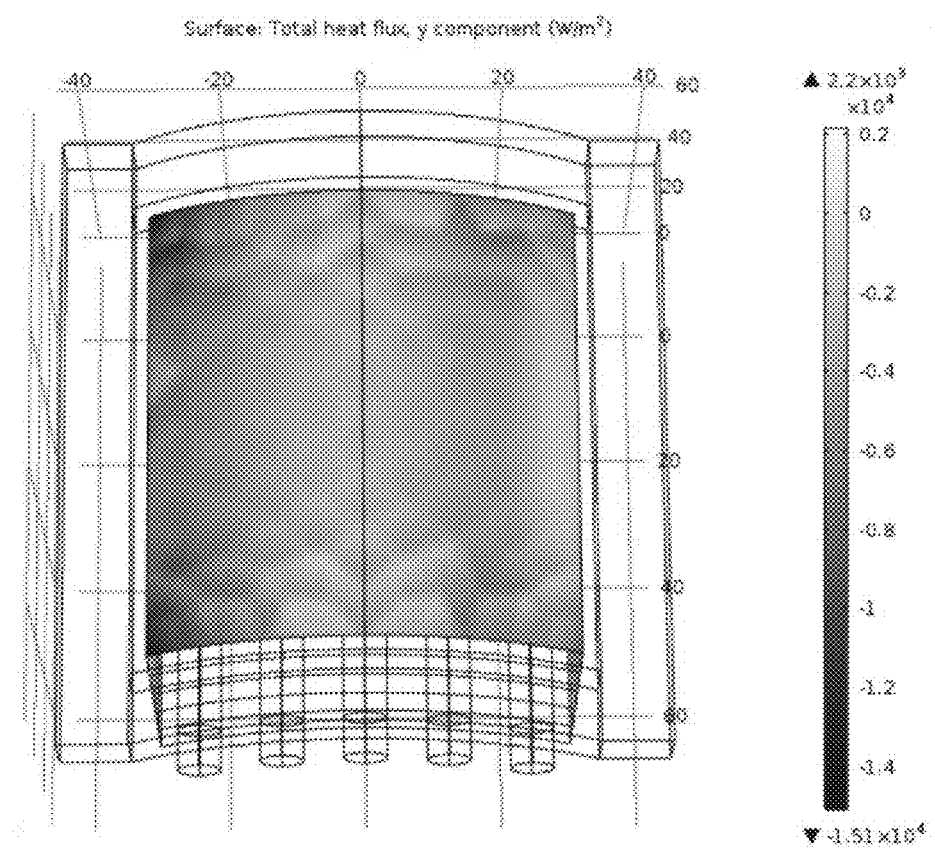
Figure 8A:
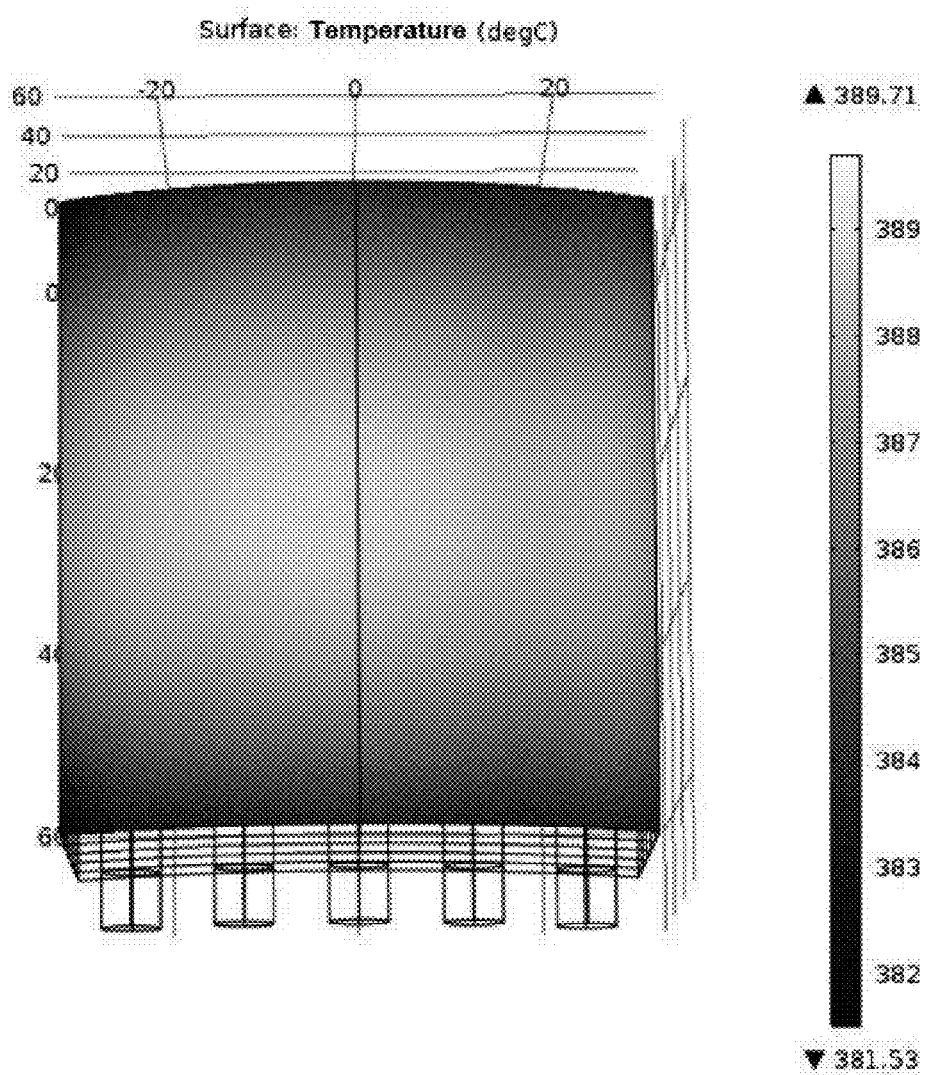
FIGS. 8A and 8B are views illustrating the distribution of a surface temperature and a surface heat flux of a high-temperature structure for measuring properties of a curved thermoelectric device to which no shielding section is applied.
Figure 8B:
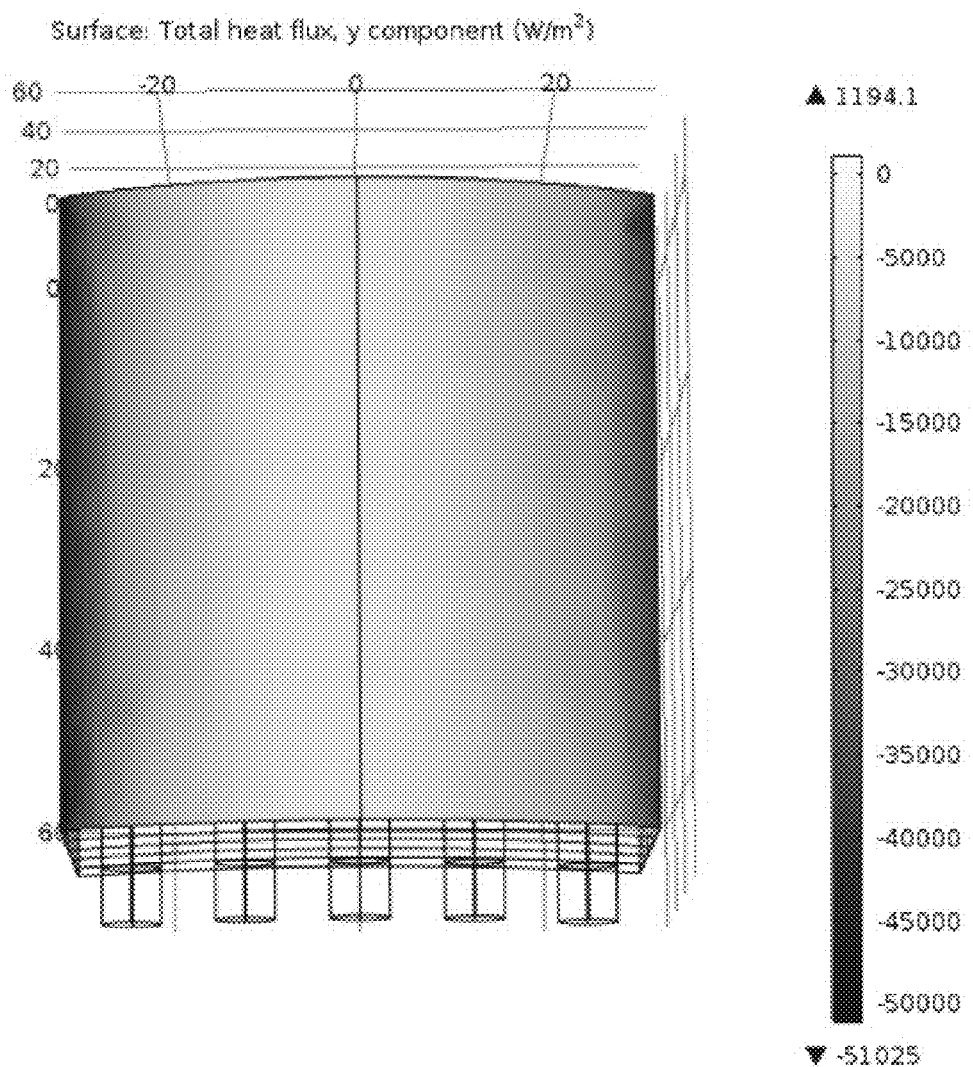

FIG. 6 is a view illustrating an embodiment of a shielding section 300a in the properties measuring system using the high-temperature structure for measuring the properties of the curved thermoelectric device according to the embodiment of the present invention, FIGS. 7A and 7B are views illustrating the distribution of the surface temperature and the surface heat flux of the high-temperature structure for measuring the properties of the curved thermoelectric device to which the shielding section 300a of FIG. 6 is applied, and FIGS. 8A and 8B are views illustrating the distribution of a surface temperature and a surface heat flux of a high-temperature structure for measuring properties of a curved thermoelectric device to which no shielding section 300, 300a is applied. They will be described below in detail.

As illustrated in FIG. 6, the shielding section 300a has a curved frame structure that surrounds the upper portion of the side of the heating element 220. Although not shown in the drawing, the shielding section 300a may include a support means to secure it to the upper portion of the side of the heating element 220.

By surrounding the upper portion of the side of the heating element 220 with the shielding section 300*a*, it is possible to prevent heat from escaping from the surface of the heating element 220. Thus, as illustrated in FIGS. 7A and 8A, when comparing a case where no shielding section 300*a* is applied with a case where the shielding section 300*a* is applied, the latter allows the surface temperature of the heating element 220 to be uniformly distributed. That is, when the temperature of the heating element 220 is adjusted to be 400° C., it is observed that a delta value ΔT of the surface temperature is only 2.92° C. when the shielding section 300*a* is used, and the delta value is increased up to 9.54° C. when the shielding section 300*a* is not used.

In addition, since the entire side of the heating element 220 is not surrounded by the shielding section 300*a* but only the upper portion of the side of the heating element 220 is surrounded by the shielding section 300*a*, it is possible to maintain the accuracy of the heat-flux measurement value that is measured in the height direction of the heating element 220, as illustrated in FIGS. 7B and 8B, while allowing the surface temperature of the heating element 220 to be uniform.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A high-temperature structure for measuring properties of a curved thermoelectric device, the high-temperature structure comprising:
    a plurality of rod-shaped cartridge heaters;
    a heating element having a surface that is a curved surface coming into contact with a lower end of the curved thermoelectric device, having a plurality of holes for accommodating the plurality of cartridge heaters, and directly heating the lower end of the curved thermoelectric device; and
    a shielding section coupled to an upper portion among an entire portion of the curved surface of the heating element,
    wherein the shielding section is a curved frame structure surrounding only the upper portion among the entire portion of the curved surface of the heating element.

2. The high-temperature structure of claim 1, wherein the plurality of holes comprises a plurality of first holes that have the same distance from a center to the surface.

3. The high-temperature structure of claim 1, wherein the plurality of cartridge heaters comprises:
    a plurality of first rod-shaped cartridge heaters each having a first diameter; and
    a plurality of second rod-shaped cartridge heaters each having a second diameter that is smaller than the first diameter,
    wherein the plurality of holes comprises:
    a plurality of second holes accommodating the plurality of first rod-shaped cartridge heaters; and
    a plurality of third holes placed above the plurality of second holes to be located therebetween, and accommodating the plurality of second rod-shaped cartridge heaters.

4. The high-temperature structure of claim 1, further comprising:
    a heat flow meter measuring heat conductivity distribution of heat that is outputted from the plurality of cartridge heaters;
    a temperature sensor measuring surface temperature distribution of the heating element; and
    a feedback control receiving the heat conductivity distribution and the surface temperature distribution, and controlling heat-generation temperature of the plurality of cartridge heaters such that the heat conductivity distribution and the surface temperature distribution are uniform.

5. A system for measuring properties of a curved thermoelectric device, the system comprising:
    a low-temperature section having a surface that is a curved surface coming into contact with an upper end of the curved thermoelectric device, and directly cooling the upper end of the curved thermoelectric device;
    a plurality of cartridge heaters each having a rod shape;
    a heating element having a surface that is a curved surface coming into contact with a lower end of the curved thermoelectric device, having a plurality of holes for accommodating the plurality of cartridge heaters, and directly heating the lower end of the curved thermoelectric device;
    a shielding section surrounding the heating element;
    a heat-insulation section disposed on a lower end of the heating element and made of a heat insulation material; and
    a measuring section connected with both the low-temperature section and the heating element to measure thermoelectric performance of the curved thermoelectric device,
    wherein the shielding section is coupled to an upper portion among the entire portion of the curved surface of the heating element and is a curved frame structure surrounding only the upper portion among the entire portion of the curved surface of the heating element.

6. The system of claim 5, wherein the plurality of holes comprises a plurality of first holes that have the same distance from a center to the surface.

7. The system of claim 5, wherein the plurality of cartridge heaters comprises:
    a plurality of first rod-shaped cartridge heaters each having a first diameter; and
    a plurality of second rod-shaped cartridge heaters each having a second diameter that is smaller than the first diameter,
    wherein the plurality of holes comprises:
    a plurality of second holes accommodating the plurality of first rod-shaped cartridge heaters; and
    a plurality of third holes placed above the plurality of second holes to be located therebetween, and accommodating the plurality of second rod-shaped cartridge heaters.

8. The system of claim 5, further comprising:
    a heat flow meter measuring heat conductivity distribution of heat that is outputted from the plurality of cartridge heaters;
    a temperature sensor measuring surface temperature distribution of the heating element; and
    a feedback control receiving the heat conductivity distribution and the surface temperature distribution, and controlling heat-generation temperature of the plurality of cartridge heaters such that the heat conductivity distribution and the surface temperature distribution are uniform.

9. A method for measuring properties using a high-temperature structure for measuring properties of a curved thermoelectric device, using a heating element that has a surface that is a curved surface coming into contact with a lower end of the curved thermoelectric device, has a plurality of holes for accommodating a plurality of cartridge heaters, and directly heats the lower end of the curved thermoelectric device, the heating element including a shielding section coupled to an upper portion among an entire portion of the curved surface of the heating element and surrounding only the upper portion among the entire portion of the curved surface of the heating element, the high-temperature structure including a temperature sensor, a heat flow meter and a feedback controller, the method comprising:

measuring, by the temperature sensor, surface temperature distribution of the heating element;

measuring, by the heat flow meter, heat conductivity distribution of heat that is outputted from the plurality of cartridge heaters;

receiving, by the feedback controller, the heat conductivity distribution from the heat flow meter and the surface temperature distribution from the temperature sensor, and controlling, by the feedback controller, heat-generation temperature of the plurality of cartridge heaters such that the heat conductivity distribution and the surface temperature distribution are uniform;

directly cooling an upper end of the curved thermoelectric device, and directly heating a lower end of the curved thermoelectric device using the heating element; and measuring thermoelectric performance of the curved thermoelectric device.

\* \* \* \* \*